United States Patent [19]

Rude

[11] 4,250,874
[45] Feb. 17, 1981

[54] THERAPEUTIC NECK TRACTIONING DEVICE

[76] Inventor: Kennon G. Rude, 340 Seminole Dr., Boulder, Colo. 80303

[21] Appl. No.: 919,900

[22] Filed: Jun. 28, 1978

[51] Int. Cl.³ .......................... A61H 1/02; A61F 5/01
[52] U.S. Cl. .................................. 128/75; 128/25 R; 272/94
[58] Field of Search ................... 128/71, 75, 78, 84 R, 128/84 C, 87 B, 25 R, 69, 83, DIG. 23; 272/94

[56] References Cited

U.S. PATENT DOCUMENTS

| 978,760 | 12/1910 | Langworthy | 128/71 |
| 1,356,365 | 10/1920 | Hosmer | 128/75 |
| 1,508,892 | 9/1924 | Mikalsen | 128/75 |
| 1,640,519 | 8/1927 | Schaeffer | 128/69 |
| 2,783,758 | 3/1957 | Trott | 128/84 R |
| 2,791,999 | 5/1957 | Bustamonte | 128/75 |
| 3,343,532 | 9/1967 | Zumaglini | 128/75 |
| 3,768,464 | 10/1973 | Greissing | 128/75 |
| 3,926,182 | 12/1975 | Stabholz | 128/75 |
| 4,161,946 | 7/1979 | Zuesse | 128/75 |

FOREIGN PATENT DOCUMENTS

| 1024205 | 2/1958 | Fed. Rep. of Germany | 128/75 |
| 1104171 | 11/1955 | France | 128/69 |
| 7704344 | 4/1977 | Netherlands | 128/75 |
| 101512 | 11/1923 | Switzerland | 128/78 |
| 1146149 | 3/1969 | United Kingdom | 128/75 |

Primary Examiner—Robert W. Michell
Assistant Examiner—Arthur S. Rose
Attorney, Agent, or Firm—Earl C. Hancock; James R. Young

[57] ABSTRACT

Excercising through pivotal motions around the region of selected neck vertebrae is obtained by an attachment to a vertically tensioning assembly. The vertical tensioning assembly includes a yoke adapted to sit on the shoulders of the wearer with an extendible support framework, such as pneumatic cylinders, connecting the yoke with a pivotable harness arrangement suspended from over the wearer's head. The attachment is adapted to couple to the vertically extendible framework so that it can be adjusted and secured in a vertical direction. The attachment includes a neck surface engaging pad configured in the vertical direction so as to overlie a small region preferably of one vertebrae in length. The pad is configured horizontally to generally conform to the neck contour. By this relationship to the user, a fulcrum point is established at a selected vertebrae level so the wearer can exercise with pivotal motions around the selected vertebrae while the neck is in tension. The pad can be adjusted in a vertical direction to allow selection of the fulcrum point level and in a horizontal direction to conform to the individual convexity of the neck of the wearer.

12 Claims, 5 Drawing Figures

THERAPEUTIC NECK TRACTIONING DEVICE

BACKGROUND OF THE INVENTION

The present invention relates to apparatus for tensioning portions of the spinal column so as to permit therapeutic exercising of the tensioned area. More particularly, the present invention relates to apparatus for tensioning or tractioning the vertebrae of the neck in a manner that allows pivotal movement of the neck while it is in vertical tension.

It has been known for some time that various disorders associated with the spinal column can be alleviated by placing the relevant portion of the spinal column in traction. For instance, U.S. Pat. No. 2,791,999 by Bustamante shows a neck stretching device with a shoulder mounting yoke and a geared arrangement for applying upward pressure to the chin and back of the head. A similar result is obtained by a pneumatically expandable collar in U.S. Pat. No. 3,343,532 by Zumaglini. Others have suggested that the spinal column can be held in a normal orientation by a pad that generally conforms to the proper spinal column shape. U.S. Pat. No. 3,926,182 by Stabholz shows such a device including vertical and horizontal adjustability for use in the lumbar region of the spinal column. The Stabholz type of device is likewise intended to allow the user to perform some exercising while the device is in place since it has also been known that such exercising while the device is in place to establish traction can have considerable therapeutic value.

One form of conventional neck region tractioning apparatus which accomodates exercising includes a shoulder yoke with a pair of pneumatically extendible cylinders connected between this yoke and an overhead suspended harness. Still another prior art device employs a pad to engage and support a region of the spinal column at the neck with means to adjust this pad to provide alignment for the particular user. After the user is seated and the device secured to the user's head, a power source mechanically forces the head of the user to follow various rocking exercises. Such a system is shown in U.S. Pat. No. 3,768,464 by Greissing for use in conjunction with an overhead suspension harness.

It had also been suggested that beneficial results can be obtained by reducing the area of spinal column support in the lumbar region and allowing the wearer to exercise around that reduced region using a device somewhat like that shown in the aforementioned Stabholz patent. However, it has not been known in the prior art as I have now discovered that the treatment of neck vertebrae disorders can be enhanced by limiting the area of neck support to a small number of vertebrae and preferably to one vertebrae or its equivalent in length so that the selected vertebrae effectively becomes a fulcrum point level around which the patient can exercise while the neck is in tension or traction. This I have found to be particularly successful in treating so-called whiplash injuries.

SUMMARY OF THE INVENTION

The present invention is a device attachable to a conventional neck tractioning or tensioning mechanism to allow the controlled therapeutic exercising of the neck vertebrae. Such conventional neck tensioning devices typically have a mount or yoke that fits over the shoulders of the patient. In addition, a head securing assembly such as a chin and lower skull engaging harness suspended from a cross-bar is extendibly attached to the shoulder by means for causing separation between the shoulder mount and the head securing assembly thereby placing the neck vertebrae in traction.

The present invention includes an attachment to such conventional neck tractioning devices with a means having a face for engaging the rear neck surface of the wearer. This face has a first dimension corresponding to the length of a selected but small number of neck vertebrae and a second dimension generally configured to conform to the rear surface of the neck transverse to the line of vertebrae. The aforementioned neck engaging means is attached to the selectably extendible means of the tractioning device so as to establish the face first dimension in a head-to-shoulders fulcrum point or level relative to the selected number of vertebrae of the wearer's neck. This structure allows the therapeutic exercising around the fulcrum point or level while the neck tractioning device is applying tensile force to the neck of the user.

The attachment can be arranged so that its postion along the extendible means is adjustable thereby accommodating the particular neck vertebrae selection and also the variations in physical length of the spinal column of different users. The neck engaging means can be arranged to be adjustable towards and away from the user's neck so as to contol the amount of pressure applied to the selected vertebrae. Preferably the neck engaging means is connected by a pivotable connection at the end of the attaching rod to accommodate pivotal exercising by the user with the selected vertebrae at the fulcrum point or level.

The foregoing and other objects, features, applications and advantages of the present invention will be readily apparent in view of the following detailed description of the exemplary preferred embodiment taken in conjunction with the accompanying drawings.

DETAILED DESCRIPTION OF THE PREFERRED EMBODIMENT

Figure 1:
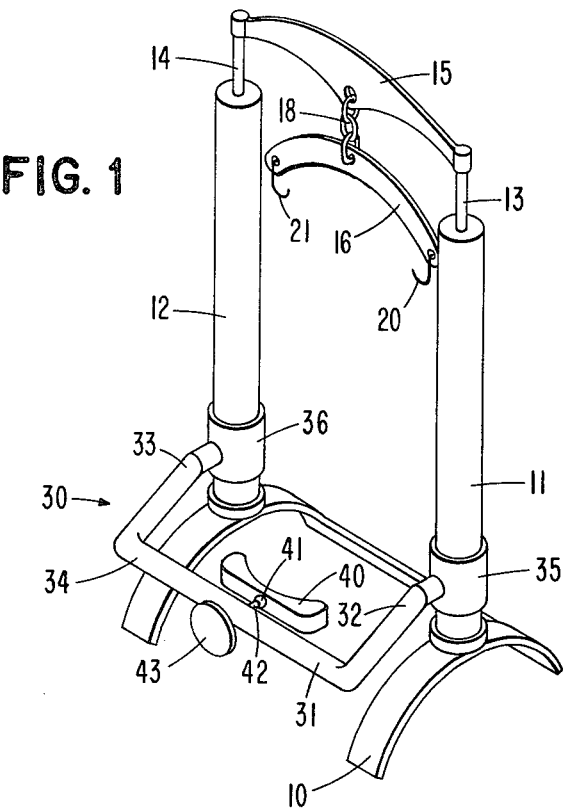
FIG. 1 is a perspective view of a neck tractioning device including structure in accordance with this invention.
Figure 2:
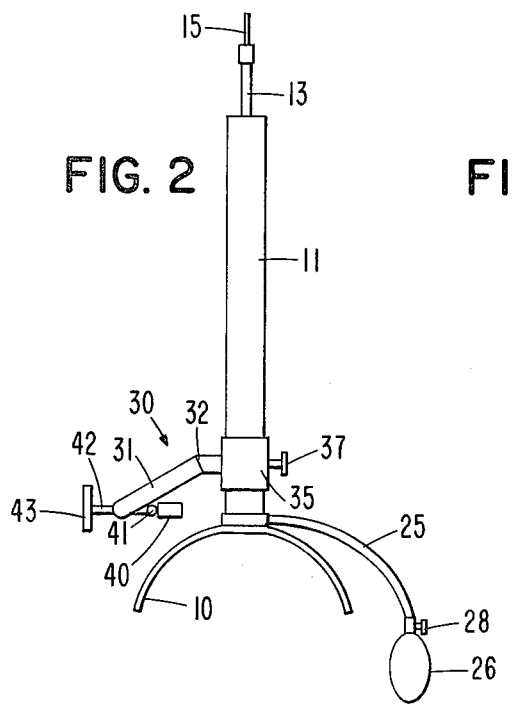
FIG. 2 is a side view of the FIG. 1 embodiment.
Figure 3:
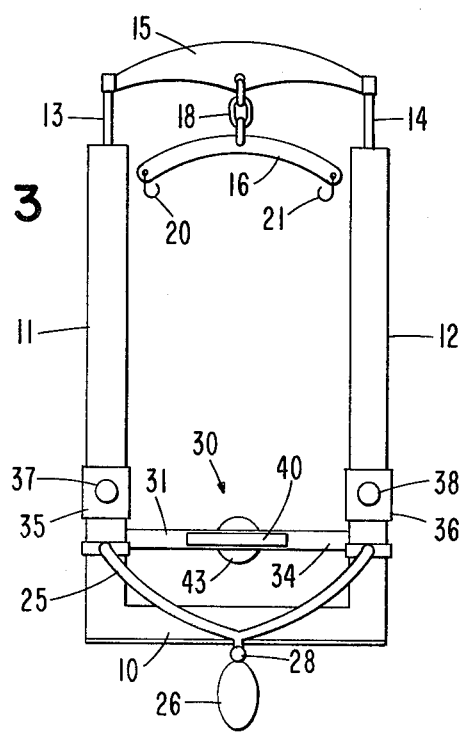
FIG. 3 is a front view of the FIG. 1 embodiment.

The embodiment of the invention in accordance with FIGS. 1–5 is shown and will be described in conjunction with a so-called Kuhlmann apparatus which is used for ambulatory treatment of cervical fractures and the like. However, it will be understood that the invention is not limited to this particular structure. The conventional Kuhlmann type device includes a curved yoke 10 which fits over the shoulders of the patient or wearer. Two upstanding generally parallel elements shown in the form of pneumatic cylinders 11 and 12 are rigidly attached to yoke 10. The plungers or piston rods 13 and 14 of cylinders 11 and 12, respectively, are connected to a cross-bar 15 which has a spreader bar 16 suspended therefrom by a ring coupler 18. The outer ends of bar 16 have hooks 20 and 21 from which a harness or head sling 22 (note FIG. 4) can be suspended. Pneumatic cylinders 11 and 12 are selectably extended or retracted by a split tube 25 commonly actuated by a squeeze bulb 26 and exhausted via relief valve 28 as best seen in FIGS. 2 and 3. It should be understood that the structure described thus far in this detailed description is conventional and is sometimes known in commercial sources as a Kuhlmann Cervicle Brace.

The fulcrum establishing attachment assembly 30 in accordance with this invention includes a generally U-shaped member 31 attached to the cylinders 11 and 12 by means of slidable collars 35 and 36. Collars 35 and 36 preferably can be removed and attached through the agency of a hinged clamp design but with means for securing them in the selected vertical position as by thumb screws 37 and 38 or the like. A padded element 40 is coupled by a ball joint 41 to a bolt 42 which is threaded through the center of the rear extension of U-member 31. An adjusting wheel or knob 43 allows horizontal positional selection so as to control the pressure on the neck of the user at the fulcrum point or level. Note that threaded screw 42 and knob 43 can be replaced with another pneumatic cylinder with its own actuating bulb and relief valve.

Figure 4:
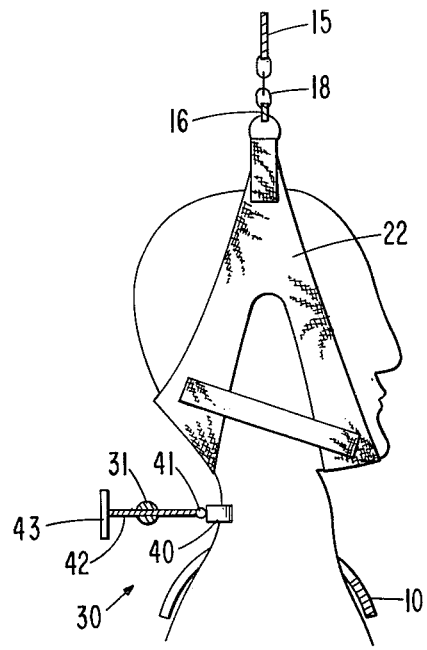
FIG. 4 is a side, partially sectioned view of the FIG. 1 embodiment showing its operative relationship to a patient or user.

Pad 40 is preferably formed of a relatively rigid backing plate with a contoured padding of flexible material such as nylon, polyurethane foam, rubber or the like forming the interface for engaging the back of the user's neck. Ideally, pad 40 has a first dimension in the direction of the cervical spinal column (ie: vertically as shown in FIGS. 2, 3 and 4) which approximately conforms to the height of one vertebrae. However the vertical height of pad 40 can be of a greater or even lesser distance than a single vertebrae as long as a selected vertebrae region or level becomes established as a fulcrum around which the patient can perform pivotal exercises while the neck is in traction. This pivotal movement is accommodated by ball joint 41. The second dimension of pad 40 transverse to the line of the cervical spinal column (ie: horizontal as shown in FIGS. 2-4) generally conforms to the contour of the neck and essentially prevents the wearer from moving laterally from the desired established fulcrum level or point. When positioned against the neck, as shown in FIG. 4, pad 40 is symmetrically oriented about the vertebral line so that uniform pressure may be applied to the neck over the region of contact.

Note that cross-bar 31 is configured with a slightly downward bow so that pad 40 can be positioned to engage vertebrae even below the upper part of the wearer's shoulders. This bow is formed in a plane oblique to the plane of the upstanding elements. Without such bow collar or yoke 10 when in place on a patient would normally only allow pad 40 to engage the surface of the wearer's neck at a point slightly above the horizontal uppermost portions of the wearer's shoulders. However, the slight downward orientation of crossbar 31 permits selection of vertebrae at the very lowest region of the neck for pivotal exercising. This downward sloping of crossbar 31 can be avoided if yoke 10 is arranged to have vertical mounting posts or columns for slidable collars 35 and 36 positioned on the lower rear extremity of yoke 10 provided a proper secured relation is established relative to suspension bar 15.

Figure 5:
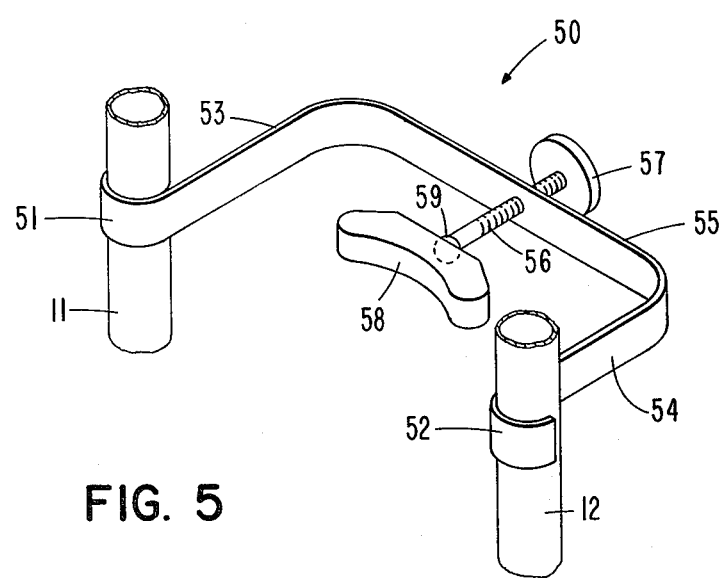
FIG. 5 is a perspective view of another form of attachment structure in accordance with the present invention.

FIG. 5 illustrates a modification of the cross-bar which is particularly advantageous for economy of manufacture. A single elongated flat plate 50 is bent into a U-shaped configuration but with the outer ends 51 and 52 of side portions 53 and 54 formed so as to hook over cylinders 11 and 12 as shown. A threaded rod 56 is screwed through rear portion 55 and extended or retracted via knob 57. A padded member 58 having a neck surface engaging face configured as described previously is coupled to rod 56 by ball joint 59. Thus the hook ends 51 and 52 can be slipped over cylinders 11 and 12 and the pad 58 extended to apply rearward pressure on elongated plate 50 thereby holding the device in its proper vertical orientation.

In use, the collar 10 is placed over the patient's shoulders with head sling 22 positioned to secure the chin and rear portion of the head as shown in FIG. 4. The pneumatic cylinders 11 and 12 are pressurised by bulb 26 with relief valve 28 closed thus imparting traction to the neck. The U-member 31 or 50 is vertically positioned on the cylinders 11 and 12 and the pad 40 or 58 is adjusted so that a selected vertebrae is under the pad thus establishing a fulcrum at this selected vertebrae. The patient then performs rotary or pivotal exercises relative to the normal three axes of movement around the selected vertebrae due to the engagement of the pad. This results in relaxation of the neck muscles and the regions associated with the cervical vertebrae. This exercising with the present invention in use has been found to significantly enhance recovery by patients suffering from disorders or injuries in the cervical region.

In a typical implementation, the cylinders 11 and 12 each are of $1\frac{3}{8}$ inch outer diameter and the slidable collars 35 and 36 have a slightly greater inner diameter with an appropriate sized thumb screw 37 and 38 for securing the attachment in place. The cross-bar 31 is an aluminum bar bent with a $3\frac{1}{4}$ inch horizontal extension behind the cylinders 11 and 12. That is, side arms 32 and 33 extend horizontally by $3\frac{1}{4}$ inches from the collars 35 and 36 and then extend for 3 inches in a downward direction as shown. Accordingly the horizontal line on which bolt 42 travels is actually $2\frac{1}{2}$ inches below the horizontal on which side arms 32 and 33 attach to collars 35 and 36. The pad 40 is formed of nylon materials bonded to a backing plate of 1 inch by $3\frac{3}{4}$ inches. The vertical dimension of pad 40 was the same as the backing plate as was the horizontal dimension. However, the pad 40 was formed with an arc of radius of about $2\frac{3}{8}$ inches. A bolt member 42 of fourteen threads per inch and 0.50 inch diameter permitted horizontal position control for pad 40. The rear portion 34 of cross-bar 31 was 11 inches across to accommodate the spacing between cylinders 11 and 12. Slidable collars 35 and 36 were of the split ring variety with a hinged portion to permit clamping over the outer cylinders 11 and 12 with a locking nut to hold them in place once in surrounding position over the cylinders.

Although the present invention has been described with particularity relative to the foregoing detailed description of the exemplary preferred embodiment, various modifications, additions, changes and applications other than those specifically mentioned herein will be readily apparent to those having normal skill in the art without departing from the spirit of this invention.

What is claimed is:

1. In apparatus for allowing controlled therapeutic exercising including a neck tractioning device having a shoulder mount, an assembly pivotally securable to a wearer's head and a support framework interconnecting the shoulder mount and head securing assembly having extendable means for selectably separating the shoulder mount and head assembly the improvement comprising:

means having a face for engaging the rear neck surface of the wearer with said face having a first dimension in a direction parallel to the line of vertebrae and a second dimension generally configured to conform to the rear surface of the neck transverse to the line of vertebrae, the length of said face along said first dimension being less than its length along said second dimension, and attaching means rigidly attaching said neck engaging means to said framework for establishing said engaging means face first dimension in a head-to-head shoulders fulcrum relative to said neck vertebrae for the wearer whereby therapeutic pivotal exercises are performable around said fulcrum by the wearer while the neck tractioning device is applying tensile force to the neck of the wearer, said attaching means including a pair of collars slideably mounted on said framework such that said collars are adjustable in a direction substantially parallel to the direction of separation between the shoulder mount and head assembly and securing means associated with said collars for releasably securing said collars in fixed relation to said framework and a rigid U-shaped bar having its opposite ends each secured to a respective one of said collars and adapted for surrounding the rear of the neck in spaced apart relation thereto, said neck engaging means being mounted on said bar such that when said apparatus is worn said neck engaging means is positioned between said bar and the rear surface of the neck.

2. In apparatus in accordance with claim 1 wherein said attaching means further includes means for adjusting the positioning of said neck surface engaging means in a direction generally perpendicular to the neck of the wearer.

3. In apparatus in accordance with claim 1 wherein said attaching means includes an extender rod attached to one end to said bar and a pivotally movable connection at the other end for joining said neck surface engaging means to said rod.

4. In apparatus in accordance with claim 1, wherein said U-shaped bar includes a portion extending at an oblique angle to the plane of said post members.

5. In apparatus for allowing therapeutic exercising including a neck tractioning device having a yoke adapted to fit on the shoulders of a wearer, a support framework having interconnecting extendable elements attached to the yoke and a suspension assembly attached to the support framework with the suspension assembly being adapted to accommodate a sling for the head of the wearer and the extendable elements of the support framework being adapted to adjustably separate the yoke from the suspension assembly, the improvement comprising:

an elongated bar having adjustable mounting means at each end thereof for mounting each said end to said support framework, said elongated bar including a portion configured to generally encircle the rear region of the neck of the wearer in spaced apart relation thereto, said elongated bar including adjustable positioning means associated with each said end for adjustably positioning said elongated bar at selectable positions along the support framework in a manner such that said bar is adjustable in relation to said support framework in a direction substantially parallel to the direction of separation between said yoke and said suspension assembly, means for engaging the rear neck surface of the wearer positioned between said bar and the rear surface of the wearer's neck when the apparatus is worn, said neck surface engaging means having a face for engaging the surface of the back of the neck of the wearer with said face having a first dimension parallel to the line of vertebrae of the wearer, said face being dimensioned and configured in a direction transverse to the vertebrae line for generally conforming to the contour of the neck, the length of said face in said direction transverse to the vertebrae line being larger than the length of said face in said first dimension, and means attaching said neck engaging means to said elongated bar in extended relation toward the neck of the wearer for establishing a fulcrum around a preselected number of vertebrae for accommodating therapeutic exercising by the wearer around said fulcrum.

6. In apparatus in accordance with claim 5 wherein said attaching means includes a rod attached at one end to said bar and a ball joint at the other end connected to said neck surface engaging means.

7. In apparatus in accordance with claim 6 wherein said rod is attached to said bar by means for adjusting the position of said neck surface engaging means in a direction generally perpendicular to the line of the neck vertebrae of the wearer.

8. In apparatus in accordance with claim 5 wherein said elongated bar includes a portion extending outwardly from the plane of said parallel elements at an oblique angle thereto in a downward direction for permitting the positioning of said neck surface engaging means at a point below the yoke when positioned along the general shoulder line of the wearer.

9. In apparatus in accordance with claim 5, wherein said elongated bar is formed as a U-shaped rigid strap having outwardly projecting reverse-curved ends, each configured to receive a portion of a respective interconnecting element and frictionally secured thereto when said neck surface engaging means is positioned against the back of the neck.

10. The method for controlled therapeutic exercising of the human neck in the cervical region between the shoulder area and the head of a patient to be treated, comprising the steps of:

applying a tractive force to the head of the patient;

applying lateral pressure uniformly to a region of the neck adjacent a single preselected vertebrae, whereby the neck is placed in a head-to-shoulders fulcrum about said preselected vertebrae, said region being a surface of the back of the neck having a width elongated in a direction perpendicular to the line of the vertebrae and a height not exceeding the height of said preselected vertebrae; and manipulating the head of the patient to exert torsional forces on said preselected vertebrae.

11. The method according to claim 10, wherein said lateral pressure is applied symmetrically about the line of the vertebrae.

12. In apparatus for allowing therapeutic exercising the human neck comprising in combination:

a yoke adapted to fit on the shoulders of a wearer;

an adjustable support framework attached to and extending upwardly of said yoke;

neck tractioning means supported by said framework for adjustably applying upwardly directed traction to said neck tending to pull the wearer's head away from the shoulders, said adjustable support framework being adapted to apply said traction by adjustably extending the distance between said yoke and said neck tractioning means;

a rigid bar having its ends adjustably mounted on said framework in a manner such that said collars are adjustable in a direction substantially parallel to the direction of separation between said yoke and said neck tractioning means, said rigid bar encircling the back of the neck when the yoke is positioned on the wearer's shoulders;

a neck engaging means mounted on said bar and positioned between said bar and a wearer's neck when the apparatus is worn for engaging the rear neck surface of the wearer;

first position adjustment means associated with said neck engaging means for selectively adjusting the position of said neck engaging means in a direction generally perpendicular to the direction of separation between said yoke and said neck tractioning means; and second position adjustment means associated with said neck engaging means for selectively adjusting the position of said neck engaging means in a direction generally parallel to the direction of separation between said yoke and said neck tractioning means.

* * * * *